United States Patent [19]

Miller

[11] Patent Number: 4,589,410
[45] Date of Patent: May 20, 1986

[54] ENDOTRACHEAL TUBE

[76] Inventor: Larry S. Miller, 218 Manchester Manor, Thiboudaux, La. 70301

[21] Appl. No.: 754,969

[22] Filed: Jul. 15, 1985

[51] Int. Cl.⁴ ............................................. A61M 16/00
[52] U.S. Cl. .............................. 128/207.15; 128/657
[58] Field of Search ..................... 128/207.14, 207.15, 128/768, 772, 657

[56] References Cited

U.S. PATENT DOCUMENTS

| | | | |
|---|---|---|---|
| 3,071,161 | 1/1963 | Ulrich | 128/8 |
| 3,162,214 | 12/1964 | Bazinet, Jr. | 128/4 |
| 3,470,876 | 10/1969 | Barchilon | 128/4 |
| 3,776,222 | 12/1973 | Smiddy | 128/6 |
| 4,150,676 | 4/1979 | Jackson | 128/207.15 |
| 4,353,358 | 10/1982 | Emerson | 128/4 |

Primary Examiner—Kyle L. Howell
Assistant Examiner—Daniel Haneiwich
Attorney, Agent, or Firm—Wilkinson, Mawhinney & Theibault

[57] ABSTRACT

The present disclosure is directed to an apparatus of the endotracheal type to facilitate rapid intubation of the trachea with an endotracheal tube, with or without a laryngoscope in an operating room or under emergency field conditions where the insert end of an endotracheal tube may be selectively curled to accommodate varying physical conditions of the person to be intubated. The amount of curl imparted to the leading insert end of the endotracheal tube is controlled externally by the person intubating the patient by pulling on a ring attached to a cord within a tunnel on the outside of the tube, the end of the cord remote from the ring being attached to the tube in area above the balloon on the insert end of the tube.

1 Claim, 7 Drawing Figures

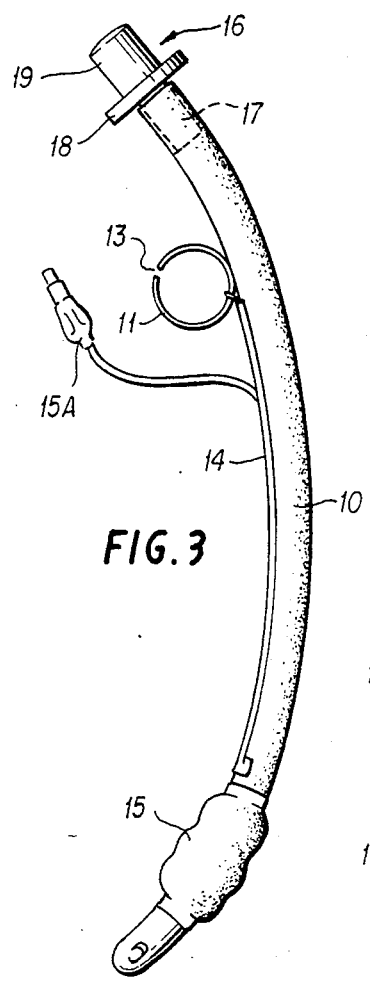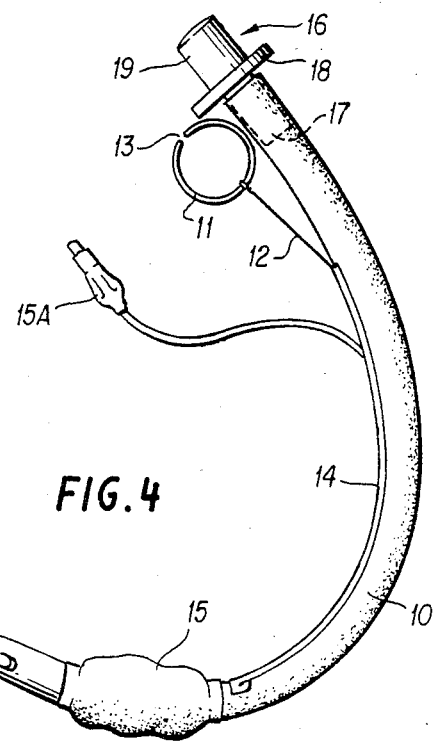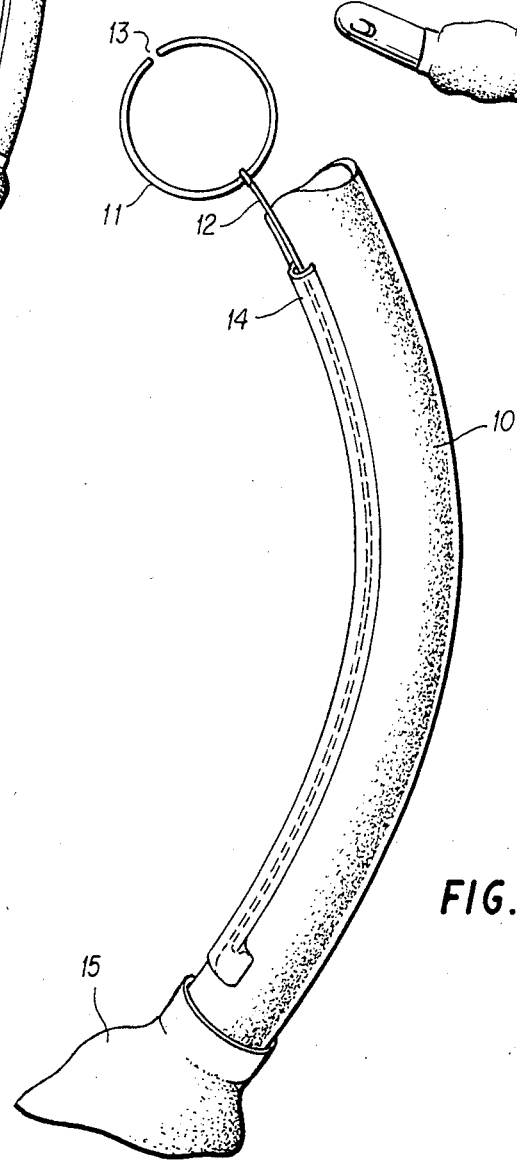
FIG.3
FIG.4
FIG.5

ENDOTRACHEAL TUBE

BACKGROUND OF THE INVENTION

Numerous apparatus have been proposed for intubation of a patient with an endotracheal tube such as the Joseph F. Smiddy U.S. Pat. No. 3,776,222 which employs fiber optics and is introduced by way of the nasopharynx. The endotracheal tube may in some instances be passed alongside the metal laryngoscope where one is available and in use but such conditions are not always available as by way of example at the scene of an auto accident.

Other apparatus for entering body cavities are U.S. Pat. No. 3,470,876 to Barchilon; U.S. Pat. No. 4,353,358 to Emerson which do not provide simple structure for controlling curvature to permit rapid intubation and a balloon structure to guard against pulmonary aspiration.

U.S. Pat. Nos. 3,071,161 Ulrich and 3,162,214 while teaching flexible tube structures do not teach simple throwaway tubes of the endotracheal type which may be used by paramedics in emergency field conditions and which once inserted and the airway established may be left in position even when the patient arrives at the emergency room or operating room of a hospital.

SUMMARY OF THE INVENTION

The prior art endotracheal tube is a cylinder shaped tube that is used as a passage way to administer oxygen and special gases to a patient. It also serves a secondary function in that it blocks the trachea and prevents pulmonary aspiration (entering of food, foreign bodies or stomach contents into the lungs). The endotracheal tube is primarily used in surgery, although its placement is of utmost importance in a vast number of emergency situations.

In surgery, the patient is rendered unconscious by administration of drugs or gases. The patient's mouth is opened and a lyringoscope blade is placed into the mouth. The blade slides down into the throat of the patient and a lifting force is applied in order to visualize the correct anatomical structures. The glottis, which is the opening between the vocal cords, is the target area in which the balloon end of the endotracheal tube of the present invention will enter the trachea. When the tube enters the glottis it is advanced into the trachea and the balloon is inflated with air to create an air tight seal of the trachea and lungs.

Patient anatomies differ greatly from one to another therefore, different tube curls may be required. In the patient with an anterior glottis (the vocal cords and glottis positioned high in the patient's neck) intubation which is the act of placing the tube through the glottis, can be extremely difficult. This condition is usually undetectable until the vocal cords and glottis are actually visualized with a lyringoscope and blade. If the endotracheal tube can not be placed through the glottis because the angle is too great another attempt must be made. Therefore the endotracheal tube of the prior art and lyringoscope blade must be withdrawn and a stylet (a semi-rigid wire) must be placed into the endotracheal tube. The stylet is then bent to the approximate angle giving the endotracheal tube an upward lift or a "U" shaped appearance. Once this is accomplished another attempt must be made and pressure on the neck is usually applied to force the glottis down decreasing the anatomical angle and facilitating the intubation process.

One must realize that this extra procedure takes more time to complete the intubation. Time is of utmost importance with patients who are in dire need of oxygen or those with full stomachs in which food could be regurgitated and aspirated into the lungs. Although both methods are used they leave much to be desired. For instance, placement of the stylet into the tube must be done either before or after the first intubation attempt has been made. The amount of bend or angle placed in the stylet is a mere guess that it will fit the patient's natural anatomy. If the angle or curvature of the endotracheal tube and stylet are too great or not great enough the intubation progress must again be terminated momentarily and the stylet and tube must be reshaped. Again keep in mind that time is a very important factor and its prolonging could be crucial to the safety of the patient.

Another danger point with the stylet is that it can be advanced beyond the balloon tip of the endotracheal tube and protrude past the end of the tube. During intubation the protruding end of the stylet could puncture delicate soft tissue. If for instance, the vocal cords were damaged it could cause a permanent speech impediment. Therefore the stylet can assist with intubations but it can also cause major complications.

The other method of obtaining difficult intubations is by applying pressure to the neck. Patients with a severe anterior placed glottis, pressure will not bring the glottis low enough to intubate. In fact, in some cases when more pressure is required to decrease the anatomical angle, it can partially collapse the glottis opening. This decreases the internal diameter of the glottis and hinders the endotracheal tube from entering the trachea because of a size misfit.

The major difference with the present invention over the prior art endotracheal tube is that the balloon end of the tube can be manually curled to meet the natural oral-tracheal curvatures of the human anatomy. This improvement creates a greater safety margin by facilitating the act of intubation. As set forth hereinabove the practice now being employed is either the placement of a stylet into the endotracheal tube or by applying pressure to the throat. Any degree of tube curl can be obtained or changed during the actual act of intubation with the present invention. This is accomplished manually with minimal amount of dexterity and without removing the tube from the mouth. Therefore guess work is eliminated.

The tube of the present invention is similar in appearance to a regular inflatable endotraceal tube, except for a few functional differences. My tube is designed with a small removable ring and a pull cord attached to the tube. The ring is an incompleted circular shape allowing a gap of approximately five millimeters for removing. The ring is attached to the cord loose enough so that it can be easily and quickly removed. With the intubation has been completed, the ring is rotated counterclockwise so that the anchoring point of the cord to the ring is shifted towards the gap in the ring. When the cord reaches the gap, the ring is released and freed from the tube. The cord can slide freely in and out without being obstructed by the walls of the tunnel. Besides the tunnel giving ample room for the cord, it also serves as a cover for the cord so that nothing interfers with the intubation process.

BRIEF DESCRIPTION OF THE DRAWINGS

FIG. 3 is a side elevational view of the endotracheal tube of the present invention in the relaxed condition prior to intubation.

FIG. 4 is a view similar to FIG. 3 showing the intubation ring pulled to impart a curl to the tube.

FIG. 5 is an enlarged fragmentary schematic view of the tube of FIGS. 3 and 4 showing the ring and cord in tunnel attachment of the cord to the endotracheal tube of the present invention.

BEST MODE FOR CARRYING OUT THE INVENTION

Figure 2:
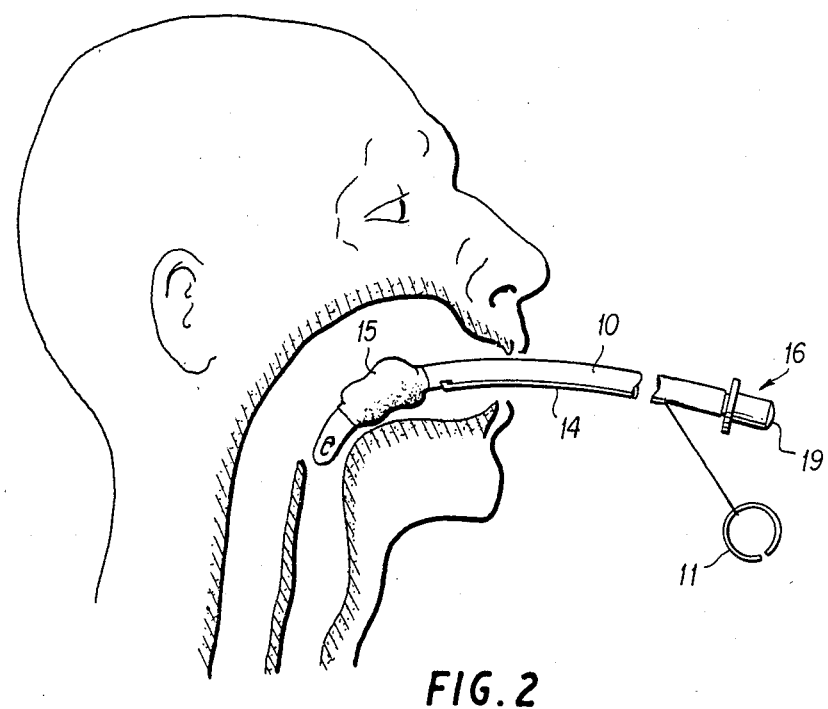
FIG. 2 is a view similar to FIG. 1 where the intubator has pulled on the ring of the tube imparting a curl to the leading end of the tube directing it toward the trachea and away from the esophagus.

The major difference between the tube of the present invention and the prior art endotracheal tube is that the balloon end of my tube can be manually curled to meet the natural oral-tracheal curvatures of the human anatomy, best seen in FIG. 2. This improvement creates a greater safety margin by facilitating the act of intubation. As stated hereinbefore, the practice now being employed is either placement of a stylet into the endotracheal tube or by applying pressure to the throat. Any degree of tube curl can be obtained or changed during the actual act of intubation with my tube. This is accomplished manually with a minimal amount of dexterity and without removing the tube from the mouth.

My tube 10 is similar in general appearance to a regular inflatable endotracheal tube. The tube 10 of the present invention has a small removable ring 11 and a pull cord 12 attached to the tube 10. The ring 11 is an incompleted circular shape allowing a gap 13 of approximately five millimeters for removing. The ring 11 is attached to the cord 12 loose enough so that it can be easily and quickly removed. When the intubation has been completed, the ring 11 is rotated counterclockwise so that the anchoring point of the cord 12 to the ring 11 is shifted towards the gap 13 in the ring. When the cord 12 reaches the gap 13, the ring 11 is released and freed from the tube. The cord can slide freely in and out without being abstructed by the walls of a tunnel 14. Besides the tunnel 14 giving ample room for the cord 12, it also serves as a cover for the cord 12 so that nothing interferes with the intubation process. The cord 12 then follows down the tunnel towards the tip of the inflatable balloon 15. When the tunnel 14 has neared the balloon 15 it terminates and at that point the cord 12 is either attached securely to the end of the tunnel 14 or directly to the tube 10.

Figure 7:
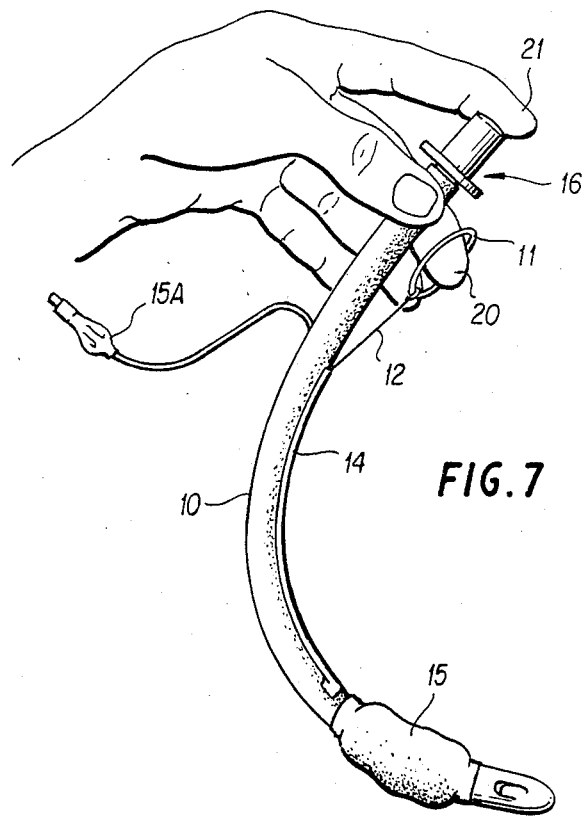

It is to be noted from FIGS. 2, 4 and 7, that when the ring 13 is pulled up towards the connector end tip 16 of my endotracheal tube 10 the balloon end will curl upward. The length of the cord 12 pulled from the tunnel 14 will determine the degree of curl desired. The greater the length of cord pulled from the tunnel, the greater the angle. The connector tip or end 16 has an insert plug 17 receivable in the open end of the tube 10, an annular limit stop 18 and a gas tube connector 19 for attaching a respiratory gas to the tube 10.

IN OPERATION

Figure 1:
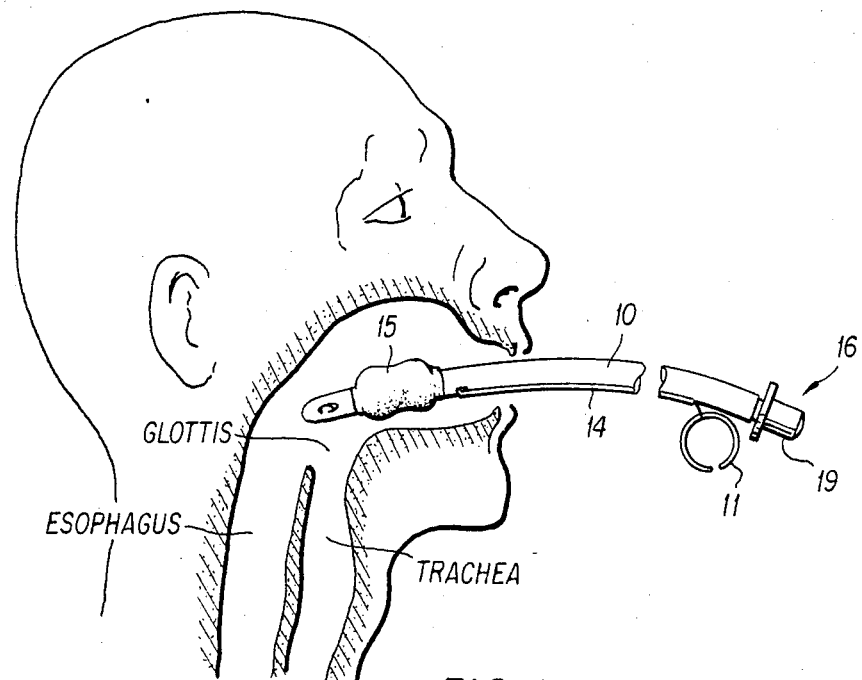
FIG. 1 is a schematic view of the endotracheal tube of the present invention being initially inserted into the mouth of a patient.
Figure 6:
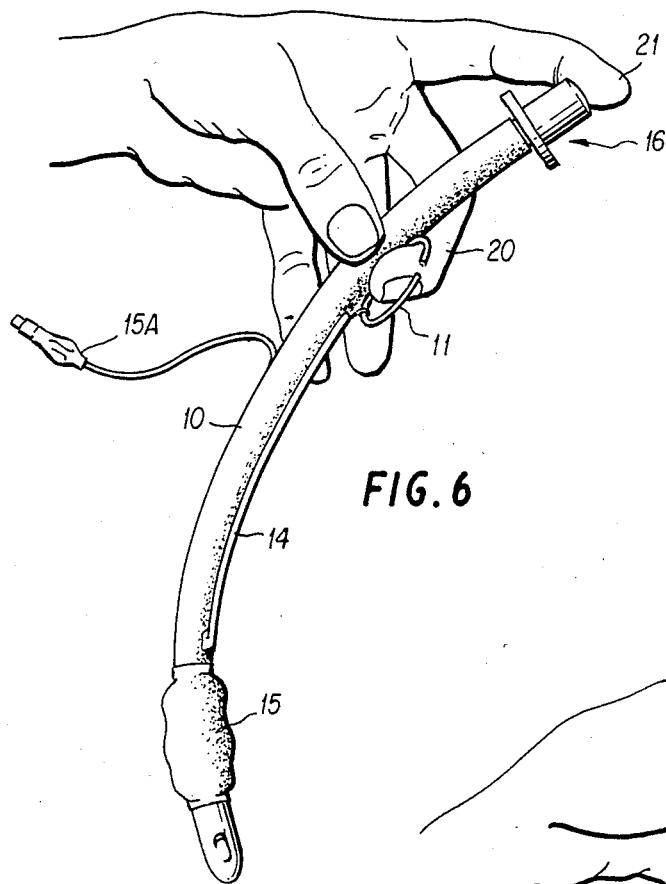
FIGS. 6 and 7 show schematically the manipulative sequence of the lefthand of the intubator in insertion of the endotracheal tube into the trachea of the patient.

FIGS. 6 and 7 illustrate the proper handling technique and grip of my tube 10. With the untriggered tube 10, the middle finger 20 is placed into the ring 11. The index finger 21 is placed on the uppermost boundary of the connector tip 16. Then the tube 10 is introduced into the patient's mouth and advanced towards the glottis as best seen in FIGS. 1 and 2. The middle finger 20 is then drawn up towards the endotracheal tube connector tip 16 using the index finger 21 for leverage, shown in FIG. 7. Again the amount of cord 12 withdrawn will determine the amount of curl. Therefore, patients with extremely anterior glottis, which normally contribute to difficult intubations, can be easily intubated by merely withdrawing more cord 12 from the tunnel 14.

The tube of the present invention provides a more reasonable and logical means of securing a difficult intubation. Instead of changing human anatomy by force to match the curl of a tube, force is applied to a tube to match the natural human anatomy, also missed attempts due to improper tube curl are eliminated because of my tube's ability to change angles instantaneously.

In the pediatric form of my tube the tube 10 is fitted with a balloon 15 having an external syringe connection 15A for the inflation of the balloon 15. In the uncuffed tube, that is one without a balloon 15, the tunnel 14 and cord 12 run on the top of the endotracheal tube 10 (as with the adult type) of the tunnel 14 and cord 12 are placed between the inner and outer walls of the endotracheal tube itself or the tunnel and cord run along the inside of the tube attached to the inner wall surface.

Among the many areas of application of my tube is the very dramatic Caesarean Section (operation involving delivery of baby by cutting into the womb). My tube would contribute greatly to the safety of the mother and fetus.

The number one cause of maternal death, as a result of a general anesthetic, is caused by pulmonary aspiration. This occurs when the stomach contents are regurgitated into the trachea and lungs. Therefore it is of momentous importance that the trachea be intubated as quickly as possible after the patient has been rendered unconscious and paralyzed. Intubation blocks off the trachea from stomach contents as well as secure an airway for oxygen and other gases. It can easily be seen that if the tube 10 does not match the anatomical curvature of the patient and the trachea can not be swiftly intubated a number of serious problems may present themselves as well as death to mother and fetus.

What I claim is:

1. An apparatus for the rapid intubation of the trachea comprising
   a hollow solid walled open ended plastic endotracheal tube having a connector tip at one end and being open and variably curvable at the other end for insertion directly into the trachea,
   an inflatable balloon carried externally of said tube proximate the open end,
   a syringe adapter for administering gas into the balloon extending externally of said hollow tube in the region of the connector tip end and being in gaseous communication with the balloon at the remote end of said tube for inflating same after insertion of the tube into the trachea, a closed tunnel externally of the solid walled tube having a closed end and an open end for selectively imparting a curl to the tube, said external tunnel extending from above the balloon to proximate to connector tip, a pull cord within said external tunnel having one end fused to the outside of the endotracheal tube over an area greater than the width of said tunnel and having its free end releasably connected to a split ring to permit removal of the ring upon completion of intubation.

* * * * *